(12) United States Patent
Perri et al.

(10) Patent No.: US 6,864,376 B2
(45) Date of Patent: Mar. 8, 2005

(54) PROCESS FOR PRODUCING ASCORBIC ACID

(75) Inventors: Steven Thomas Perri, Kingsport, TN (US); Michael Roy Cushman, Punta Gorda, FL (US); Jeffery Earl Grant Powell, Blountville, TN (US); Brendan William Boyd, Johnson City, TN (US); Bhaskar Krishna Arumugam, Kingsport, TN (US); Nick Allen Collins, Fall Branch, TN (US)

(73) Assignee: Eastman Chemical Company, Kingsport, TN (US)

( * ) Notice: Subject to any disclaimer, the term of this patent is extended or adjusted under 35 U.S.C. 154(b) by 337 days.

(21) Appl. No.: 10/036,912

(22) Filed: Dec. 21, 2001

(65) Prior Publication Data

US 2002/0147352 A1 Oct. 10, 2002

Related U.S. Application Data

(60) Provisional application No. 60/257,991, filed on Dec. 22, 2000, and provisional application No. 60/314,999, filed on Aug. 24, 2001.

(51) Int. Cl.[7] .......................................... C07D 307/62
(52) U.S. Cl. ..................................................... 549/315
(58) Field of Search ........................................ 549/315

(56) References Cited

U.S. PATENT DOCUMENTS

| | | |
|---|---|---|
| 2,265,121 A | 12/1941 | Reichstein |
| 2,462,251 A | 2/1949 | Bassford et al. |
| 2,491,065 A | 12/1949 | van Eeklelen et al. |
| 3,721,663 A * | 3/1973 | Hinkley et al. ............. 549/315 |
| 4,767,870 A | 8/1988 | Fujiwara et al. |
| 4,778,902 A | 10/1988 | Fujiwara et al. |
| 5,128,487 A | 7/1992 | Tomislav et al. |
| 5,391,770 A | 2/1995 | Le Fur et al. |
| 5,744,618 A | 4/1998 | Fechtel et al. |
| 5,817,238 A | 10/1998 | Makino et al. |
| 5,902,885 A | 5/1999 | Takanohashi et al. |
| 6,004,445 A | 12/1999 | Genders et al. |
| 6,153,791 A | 11/2000 | Moore |
| 6,197,977 B1 | 3/2001 | Böttcher et al. |
| 6,476,239 B1 | 11/2002 | Arumugam et al. |

FOREIGN PATENT DOCUMENTS

| | | |
|---|---|---|
| DE | 3843389 | 6/1990 |
| DE | 19734086 C1 | 8/1998 |
| DE | 199 04 821 C1 | 7/2000 |
| EP | 0554090 A2 | 4/1983 |
| EP | 1 048 663 A1 | 11/2000 |
| GB | 1222322 | 2/1971 |
| GB | 2034315 | 6/1980 |
| JP | 48015931 | 2/1973 |
| WO | WO 87/00839 | 2/1987 |
| WO | WO 97/13761 | 4/1997 |
| WO | WO 99/07691 | 2/1999 |
| WO | WO 00/46216 | 8/2000 |

OTHER PUBLICATIONS

BP, 428,815, Reichsten, May 20, 1935.
Anderson, S., et al., Production of 2–Keto–L–Gulonate, an Intermediate in L–Ascorbate Synthesis, by a Genetically Modified *Erwinia herbicola*, *Science*, 230, pp. 144–149, 1985.
Navarro, A., et al., Continuous chromatographic separation process: simulated moving bed allowing simultaneous withdrawal of three fractions, *J. of Chromatography A*, 770, pp. 39–50, 1997.
Reichstein, T., Eine ergiebige Synthese der 1–Ascorbinsaure (C–Vitamin)[2], *Helv. Chim. Acta* 17, pp. 311–328, 1934—no English version available—see Information Disclosure Statement for description of disclosure.
Regna, P.P., et al., Kinetics of Transformation of 2–Ketopolyhydroxy Acids, *J. Am. Chem. Soc.*, 66, pp. 246–250, 1944.
Saito, Y., Direct Fermentation of 2–Keto–L–Gulonic Acid in Recombinant *Gluconobacter oxydans*, *Biotechnol. Bioeng.*, 58 (2 & 3), pp. 309–315, 1998.
Wankat, P.C., Chapter 10.4, Simulated Moving Bed Fractionation, *Rate–Controlled Separations*, Elsevier Applied Science, NY, pp. 524–541, 1990.
Wedzicha, B.L., et al., Inhibition of Browning by Sulfites, *Adv. In Experimental Medicine and Biology*, 289, pp. 217–236, 1991.
Wedzicha, B.L., New Insight into the Mechanism of the Maillard Reaction from Studies of the Kinetics of its Inhibition by Sulfite, *Spec. Publ.—R. Soc. Chem.*, 151, pp. 82–87, 1994.
PCT Notification of Transmittal of the International Search Report for PCT/US01/49859 (filed Dec. 21, 2001), "Process for Producing Ascorbic Acid in the Presence of a Sulfit", mailed Apr. 22, 2002, and published Jul. 4, 2002.

* cited by examiner

*Primary Examiner*—Bernard Dentz
(74) *Attorney, Agent, or Firm*—Eric D. Middlemas; Bernard J. Graves, Jr.

(57) ABSTRACT

The present invention comprises the use of sulfite additives to reduce discoloration of L-ascorbic acid produced from acid or aqueous solutions of 2-keto-L-gulonic acid. In one aspect, the present invention comprises a continuous process for producing L-ascorbic acid from an aqueous solution of 2-keto-L-gulonic acid. The use of sulfite additives reduces product stream color and improves product recovery by binding to high molecular weight reaction by-products. In a continuous process, the reaction stream is separated from residual sulfite and sulfite-bound by-products to produce a product stream enriched in aqueous ascorbic acid for recovery, and an enriched 2-keto-L-gulonic acid stream which is recycled to the reactor. The in situ use of sulfite additives during the reaction increases the overall yield of L-ascorbic acid, with no loss in selectivity of the synthesis.

39 Claims, 9 Drawing Sheets

SCHEMATIC OF A SIMULATED MOVING BED UNIT

PROCESS FOR PRODUCING ASCORBIC ACID

This application claims priority to U.S. Provisional Application Ser. Nos. 60/257,991, filed Dec. 22, 2000, and 60/314,999, filed Aug. 24, 2001. The disclosure of each of these provisional applications is incorporated herein by reference.

This invention was made with United States Government support under Cooperative Research Agreement No. 70NANB5H1138 awarded by the Advanced Technology Program of the National Institute of Standards and Technology. The United States Government has certain rights in the invention.

FIELD OF THE INVENTION

The present invention relates to a process for producing ascorbic acid. Specifically, the present invention relates to the use of sulfite species for the synthesis of ascorbic acid having reduced color and improved product recovery. The invention also describes a continuous process for producing L-ascorbic acid from an aqueous solution of 2-keto-L-gulonic acid through an aqueous cyclization process in the presence of sulfite additives to generate a product stream of 2-keto-L-gulonic acid and ascorbic acid.

BACKGROUND OF THE INVENTION

L-Ascorbic acid (vitamin C) is produced commercially by combined chemical and fermentation processes starting from glucose or sorbose. A common intermediate generated in the commercial process is 2-keto-L-gulonic acid (KLG), or its protected form, diacetone-2-keto-L-gulonic acid. The conversion of 2-keto-L-gulonic acid to L-ascorbic acid may be carried out by esterification with methanol, followed by cyclization using stoichiometric amounts of a base, in a methodology derived from the original Reichstein process (T. Reichstein, A. Grussner, Helv. Chim. Acta 17, pp. 311–314, 1934). Alternatively, diacetone-2-keto-L-gulonic acid may be cyclized directly, with a loss of acetone followed by consecutive lactonization and enolization, to form ascorbic acid. Direct cyclization of diacetone-2-keto-L-gulonic acid requires extensive purification for recovery of the acetone and other by-products generated.

Modifications to the Reichstein process have focused on removal or simplification of many of the chemical processing steps required for the production of 2-keto-L-gulonic acid. Improvements include controlled esterification of 2-keto-L-gulonic acid and subsequent removal of unesterified starting material (U.S. Pat. No. 5,128,487), as well as improved integration of esterification with subsequent cyclization (U.S. Pat. No. 5,391,770).

Efforts have also been directed to acid catalysis (e.g. U.S. Pat. No. 2,462,251; GB 1,222,322; GB 2,034,315; DE 3843389; WO 99/07691; and WO 00/46216) thereby removing the steps of esterification with subsequent based-catalyzed cyclization and reprotonation of the L-ascorbic acid product. In addition, modifications to improve the process such as the use of organic solvents and surfactants have been described (see e.g. U.S. Pat. No. 5,744,618; WO 98/00839; and JP-B 73015931).

An alternative means of producing ascorbic acid from 2-keto-L-gulonic acid involves an aqueous intramolecular cyclization process without the use of copious amounts of acid catalysts (T. Reichstein, Helv. Chim. Acta 17, 1934, pp. 311–328 and BP 428,815). Although aqueous cyclization does not require the extensive purification steps associated with acid catalysis, non-acid catalyzed intramolecular cyclization is associated with relatively low yields. For example, 2-keto-L-gulonic acid may be heated in water saturated with carbon dioxide with a 50% yield after fractional crystallization (U.S. Pat. No. 2,265,121). Also, 2-keto-L-gulonic acid or derivatives of 2-keto-L-gulonic acid may be heated to 130–140° C. in water to generate ascorbic acid with yields approximating 50% (U.S. Pat. No. 2,491,065).

A common problem encountered with conversion of 2-keto-L-gulonic acid to ascorbic acid in water or the presence of acidic solutions is the production of colored solutions from degradation products. These degradation products generally include high molecular weight compounds that accumulate as a function of conversion. Thus, with increasing conversion, solutions tend to become increasingly colored and eventually form insoluble by-products. Generally, methods to decolor ascorbic acid involve adsorption of the colored by-products using carbon or other solid supported agents. Ultimately, the use of large amounts of carbon or other solid decolorizing agents significantly hinders subsequent purification of the L-ascorbic acid product.

Thus, there is a need for improved methods to decolor ascorbic acid produced by aqueous or acid catalysis. In addition, there is a need for a soluble decolorizing agent for those situations where solid decolorizing agents, such as carbon, cannot be used. For example, in highly discolored solutions, the amount of carbon required can be so high as to be impractical. Also, the use of a soluble form of decolorizing agent would be beneficial in situations where impurities are bound covalently to the high molecular weight by-products, thus allowing the colored impurities to be removed by a separate step. By simplifying recovery protocols, soluble additives or agents suitable for removing colored bodies in situ significantly improve ascorbic acid yield.

SUMMARY OF THE INVENTION

The present invention comprises a method for producing ascorbic acid by treating a synthesis reaction comprising L-ascorbic acid with sulfites. The sulfites can function both as a catalyst and as a decolorization aid to simplify product purification.

Thus, in one aspect, the present invention comprises a method for reducing the amount of colored by-products in L-ascorbic acid synthesized from 2-keto-L-gulonic acid or derivatives of 2-keto-L-gulonic acid comprising adding a sulfite species to a synthesis reaction comprising conversion of starting material comprising 2-keto-L-gulonic acid or derivatives of 2-keto-L-gulonic acid to L-ascorbic acid and allowing the sulfite species to interact or react with colored by-products in the synthesis. Generally, the sulfite species comprise $SO_2$, $HSO_3^-$, $SO_3^{2-}$, $S_2O_3^{2-}$, $S_2O_4^{2-}$, and $S_2O_5^{2-}$, with sulfurous acid being a preferred source of sulfite.

In another aspect, the invention comprises a continuous process for manufacturing L-ascorbic acid comprising the steps of:

(a) heating an aqueous solution of starting material comprising 2-keto-L-gulonic acid or a derivative of 2-keto-L-gulonic acid in a reactor in the presence of at least one sulfite species under conditions such that L-ascorbic acid is generated;

(b) continuously removing from the reactor a post-reaction solution comprising unreacted 2-keto-L-gulonic acid starting compound and L-ascorbic acid;

(c) removing at least a portion of sulfur containing compounds from the post-reaction solution;

(d) removing at least a portion of the L-ascorbic acid from the post reaction solution; and (e) recycling unreacted 2-keto-L-gulonic acid compound back to the reactor.

In an embodiment, five-zone simulated moving bed (SMB) chromatography is used to couple removal of low-level sulfur products and the separation of ascorbic acid and 2-keto-L-gulonic acid starting material in a one-step process.

The foregoing focuses on the more important features of the invention in order that the detailed description which follows may be better understood and in order that the present contribution to the art may be better appreciated. There are, of course, additional features of the invention which will be described hereinafter and which will form the subject matter of the claims appended hereto. It is to be understood that the invention is not limited in its application to the specific details as set forth in the following description and figures. The invention is capable of other embodiments and of being practiced or carried out in various ways.

Thus, it is an object of present invention to provide a means for producing ascorbic acid having reduced color by employing sulfites in the conversion of 2-keto-L-gulonic acid or derivatives of 2-keto-L-gulonic acid such as the methylester of 2-keto-L-gulonic acid or the bisacetonide of 2-keto-L-gulonic acid. The sulfites may be added during the recovery of ascorbic acid by crystallization (i.e. after conversion) or in situ (i.e. during conversion of 2-keto-L-gulonic to ascorbic acid in an aqueous process). The sulfite may be added as an acid catalyst or in addition to other catalysts. Removal of the sulfite by-products may then be carried out by ion exchange, 5-zone simulated moving bed (SMB) chromatography, or other means of separation, so that the ascorbic acid can be further recovered through crystallization.

BRIEF DESCRIPTION OF THE DRAWINGS

Various features, aspects, and advantages of the present invention will become more apparent with reference to the following description, appended claims, and accompanying drawings.

DETAILED DESCRIPTION OF THE INVENTION

Figure 1:
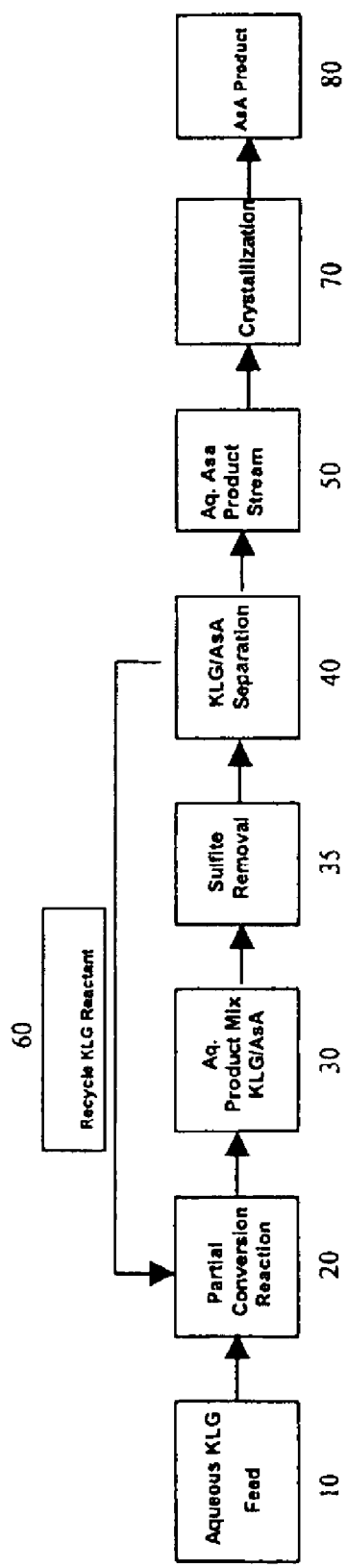
FIG. 1 is a schematic representation of the overall process for removal of sulfite from a post-reaction stream comprising 2-keto-L-gulonic acid (KLG) and L-ascorbic acid (AsA) and subsequent purification of L-ascorbic acid from recycled unreacted 2-keto-L-gulonic acid in accordance with an embodiment of the present invention.

The present invention describes the use of sulfite species for the synthesis of ascorbic acid having reduced color and improved product recovery. The sulfite species may be added in situ (i.e. during the conversion of 2-keto-L-gulonic acid to L-ascorbic acid), to prevent the build-up of colored, high molecular weight by-products and thus increase the overall yield of L-ascorbic acid. Sulfites can complex with aldehydes, carbon-carbon double bonds, and conjugated carbonyl systems which comprise colored by-products of the reaction. Upon treatment with sulfite species the ascorbic acid product exhibits substantially less coloration. The invention also describes a continuous process for producing ascorbic acid from an aqueous solution of 2-keto-L-gulonic acid using an aqueous cyclization process in the presence of sulfite additives to generate a product stream of 2-keto-L-gulonic acid and decolorized ascorbic acid.

Thus, in one aspect, the invention comprises a method for reducing the amount of colored by-products in L-ascorbic acid synthesized from 2-keto-L-gulonic acid or derivatives thereof comprising adding a sulfite species to a synthesis reaction comprising conversion of starting material comprising 2-keto-L-gulonic acid or derivatives thereof to L-ascorbic acid and allowing the sulfite species to interact or react with colored by-products in the synthesis.

In an embodiment, the sulfite species is added to the synthesis prior to conversion of the 2-keto-L-gulonic acid starting compound to L-ascorbic acid. In another embodiment, the sulfite species is added to the synthesis after conversion of at least part of the 2-keto-L-gulonic acid compound to L-ascorbic acid product. In an embodiment, the method comprises separating an L-ascorbic acid product from the synthesis reaction.

Preferably, the sulfite species comprises $SO_2$, $HSO_3^-$, $SO_3^{2-}$, $S_2O_4^{2-}$, and $S_2O_5^{2-}$. More preferably, the sulfite species comprises sulfurous acid. In an embodiment, the sulfite species may also act as a catalyst for the conversion.

Preferably, the sulfite is added to a final concentration comprising a range of 0.5% to 50% by moles, and more preferably, 1% to 20% by moles, relative to the 2-keto-L-gulonic acid compound.

In an embodiment, the 2-keto-L-gulonic acid comprises an aqueous stream from a fermentation process for producing 2-keto-L-gulonic acid. In another embodiment, the 2-keto-L-gulonic acid comprises hydrolysis of the bisacetonide of 2-keto-L-gulonic acid or the esters of 2-keto-L-gulonic acid.

Preferably, the synthesis of L-ascorbic acid from 2-keto-L-gulonic acid comprises an aqueous solution of 1 to 40 weight percent 2-keto-L-gulonic acid. More preferably, the synthesis comprises an aqueous solution of 5 to 30 weight percent 2-keto-L-gulonic acid. Even more preferably, the synthesis comprises an aqueous solution of 8 to 15 weight percent 2-keto-L-gulonic acid.

Also preferably, the conversion of 2-keto-L-gulonic acid substrate to L-ascorbic acid product preferably ranges from 5 to 95%. More preferably, the conversion of 2-keto-L-gulonic acid substrate to L-ascorbic acid product ranges from 20 to 75%. Even more preferably, the conversion of 2-keto-L-gulonic acid substrate to L-ascorbic acid product ranges from 30 to 60%.

In one aspect, the method comprises a continuous process for manufacturing L-ascorbic acid comprising the steps of:
(a) heating an aqueous solution of starting material comprising 2-keto-L-gulonic acid or a derivative of 2-keto-L-gulonic acid in a reactor in the presence of at least one sulfite species under conditions such that L-ascorbic acid is generated;
(b) continuously removing from the reactor a post-reaction solution comprising unreacted 2-keto-L-gulonic acid compound and L-ascorbic acid;
(c) removing at least a portion of sulfur containing compounds from the post-reaction solution;
(d) removing at least a portion of the L-ascorbic acid from the post reaction solution; and
(e) recycling unreacted 2-keto-L-gulonic acid compound back to the reactor.

Preferably, the sulfite species comprises $SO_2$, $HSO_3^-$, $S_2O_3^{2-}$, $SO_3^{2-}$, $S_2O_4^{2-}$, and $S^2O_5^{2-}$. More preferably, the sulfite species comprises sulfurous acid. Also preferably, the sulfite species comprises a catalyst for the conversion of 2-keto-L-gulonic acid to L-ascorbic acid.

In an embodiment, the sulfite is added to a final concentration comprising a range of 0.5% to 50% by moles, and more preferably, 1% to 20% by moles relative to the 2-keto-L-gulonic acid compound.

In an embodiment, the 2-keto-L-gulonic acid comprises an aqueous solution from a fermentation process for producing 2-keto-L-gulonic acid. In another embodiment, the 2-keto-L-gulonic acid comprises an aqueous solution of 2-keto-L-gulonic acid derived from the hydrolysis of the bisacetonide of 2-keto-L-gulonic acid or the esters of 2-keto-L-gulonic acid.

Preferably, the synthesis of L-ascorbic acid from 2-keto-L-gulonic acid comprises an aqueous solution of 1 to 40 weight percent 2-keto-L-gulonic acid. More preferably, the synthesis comprises an aqueous solution of 5 to 30 weight percent 2-keto-L-gulonic acid. Even more preferably, the synthesis comprises an aqueous solution of 8 to 15 weight percent 2-keto-L-gulonic acid.

Also preferably, the conversion of 2-keto-L-gulonic acid substrate to L-ascorbic acid product preferably ranges from 5 to 95%. More preferably, the conversion of 2-keto-L-gulonic acid substrate to L-ascorbic acid product ranges from 20 to 75%. Even more preferably, the conversion of 2-keto-L-gulonic acid substrate to L-ascorbic acid product ranges from 30 to 60%.

The sulfur containing compounds of step (c) may comprise residual sulfite, and/or sulfite bound by-products. In an embodiment, the sulfur containing compounds of step (c) comprise sulfate. Thus, the conditions used for synthesis of L-ascorbic acid results in the formation of residual acid by-products which include various poly-acid compounds as well as sulfur containing compounds. For example, some oxidation of sulfite species or sulfur compounds can occur in situ and result in the formation of sulfate species or sulfuric acid. Still, in a preferred embodiment, all of the sulfur containing compounds are removed by the separation of step (c).

In an embodiment, step (c) of the continuous process comprises removing the removing residual sulfite and sulfite bound by-products by adsorption with a solid matrix. Preferably, activated carbon is used as the adsorption matrix. Also preferably, ion exchange resin is used as the adsorption matrix.

In an embodiment, step (d) comprises continuously separating L-ascorbic acid from unreacted 2-keto-L-gulonic acid in the post reaction solution to form an L-ascorbic acid rich solution and a solution rich in 2-keto-L-gulonic acid compound. As used herein, the phrase "L-ascorbic acid rich solution" refers to an aqueous solution of L-ascorbic acid in which the ratio of L-ascorbic acid to 2-keto-L-gulonic acid has been increased relative to the post-reaction solution of step (b). Likewise, the phrase "2-keto-L-gulonic acid rich solution" or "solution rich in 2-keto-L-gulonic acid compound" refers to an aqueous solution of 2-keto-L-gulonic acid or derivatives thereof in which the ratio of 2-keto-L-gulonic acid compound to L-ascorbic acid product has been increased relative to the post-reaction solution of step (b). As used herein, derivatives of 2-keto-L-gulonic acid may comprise esters of 2-keto-L-gulonic acid, diacetone-2-keto-L-gulonic acid, and other derivatives of 2-keto-L-gulonic acid which may be cyclized to L-ascorbic acid.

In an embodiment, the method also comprises the additional step of separating the L-ascorbic acid from the L-ascorbic acid rich solution by crystallization.

The separation of the 2-keto-L-gulonic acid rich solution from the L-ascorbic acid is preferably highly efficient in the continuous process. In an embodiment, and on a 2-keto-L-gulonic acid and ascorbic acid only basis, the L-ascorbic acid rich solution of step (d) preferably comprises at least 75 weight percent of L-ascorbic acid, more preferably, at least 85 weight percent of L-ascorbic acid, and even more preferably, at least 90 weight percent of L-ascorbic acid. Also, on a 2-keto-L-gulonic acid and ascorbic acid only basis, the solution rich in 2-keto-L-gulonic acid rich compound of step (d) is preferably comprised of at least 75 weight percent of 2-keto-L-gulonic acid, more preferably, at least 85 weight percent of 2-keto-L-gulonic rich acid, and even more preferably, at least 90 weight percent of 2-keto-L-gulonic acid.

The purities for the separation of the 2-keto-L-gulonic acid compound and the ascorbic acid product are on a 2-keto-L-gulonic acid and ascorbic acid only basis, and therefore, exclude water as well as impurities arising from the KLG feed broth or reactor byproducts. These impurities may account for about 25 to 30 wt % of the total solids in the extract and raffinate products. Still, in a preferred embodiment, the separation of KLG and AsA is so effective that the AsA purity in the extract is nearly identical to the KLG recovery in the raffinate, indicative of the high purity of both fractions.

Using the continuous process described above, steps (a) through (e) preferably comprise at least a 50 mole percent yield of L-ascorbic acid. More preferably, steps (a) through (e) comprise at least a 60 mole percent yield of L-ascorbic acid. Also, the weight ratio of 2-keto-L-gulonic acid to L-ascorbic acid is preferably from 0.1 to 10, more preferably from 0.2 to 5, and even more preferably from 1 to 3, in the post reaction solution.

In an embodiment, step (d) comprises separation of L-ascorbic acid from unreacted 2-keto-L-gulonic acid in the post reaction solution by crystallization, chromatography, or electrodialysis. Preferably, ion exclusion is used for separation of L-ascorbic acid from unreacted 2-keto-L-gulonic acid in the post reaction solution. Also preferably, simulated moving bed (SMB) chromatography is used to effect this chromatographic separation.

In another embodiment, steps (c) and (d) comprise simultaneous separation and removal of residual sulfur containing compounds with the separation and segregation of L-ascorbic acid and unreacted 2-keto-L-gulonic acid. Preferably, where steps (c) and (d) comprise simultaneous separation and removal of residual sulfur containing compounds with the separation and segregation L-ascorbic acid, the method utilizes ion exclusion chromatography. Also preferably, five-zone simulated moving bed (SMB) chromatography is used to effect this chromatographic separation between sulfur containing compounds, L-ascorbic acid, and 2-keto-L-gulonic acid.

In another aspect, the present invention comprises an ascorbic acid product which has been generated in the presence of, and/or treated with, sulfites. In one aspect, the present invention comprise an ascorbic acid product having reduced coloration. The ascorbic acid product may comprise ascorbic acid which has been treated with sulfites in situ during the synthesis reaction, or which is treated by exposure to sulfites after synthesis is complete.

Thus, in one aspect, the present invention comprises L-ascorbic acid having reduced coloration and made by adding a sulfite species to a synthesis reaction comprising conversion of a starting material comprising 2-keto-L-gulonic acid or a derivative of 2-keto-L-gulonic acid to L-ascorbic acid and allowing the sulfite species to interact or react with colored by-products in the synthesis.

In yet another aspect, the present invention comprises L-ascorbic acid having reduced coloration and made by the steps of:

(a) heating an aqueous solution of starting material comprising 2-keto-L-gulonic acid or a derivative of 2-keto-L-gulonic acid in a reactor in the presence of at least one sulfite species under conditions such that L-ascorbic acid is generated;

(b) continuously removing from the reactor a post-reaction solution comprising unreacted 2-keto-L-gulonic acid starting compound and L-ascorbic acid;

(c) removing at least a portion of sulfur containing compounds from the post-reaction solution;

(d) removing at least a portion of the L-ascorbic acid from the post reaction solution; and (e) recycling unreacted 2-keto-L-gulonic acid compound back to the reactor.

Thus, the present invention describes that ascorbic acid may be obtained in high yield by thermal conversion of an aqueous solution containing 2-keto-L-gulonic acid in the presence of a sulfite species. The sulfite species functions to reduce the accumulation of high molecular weight species and reduce product solution color. In an embodiment, sulfite prevents the formation of colored by-products. Alternatively, by-products complex with the sulfite and can be removed by adsorption, ion exchange, or by ion exclusion chromatography such as five-zone SMB chromatography.

In one aspect, the present invention describes conversion of KLG in the presence of sulfites at a conversion level that maximizes the formation of ascorbic acid and recycles unreacted 2-keto-L-gulonic acid. Preferably, the separation process for ascorbic acid and 2-keto-L-gulonic acid compound is operated in such a way that an efficient separation process allows the majority of the 2-keto-L-gulonic acid to be recycled for further conversion. The product stream from the separation process may then be subjected to a recovery step, along with further decolorization using either sulfites or absorption to a solid matrix such as carbon, to obtain crystalline ascorbic acid product.

Thus, the present invention teaches the use of sulfite species that function to react with reaction by-products formed during aqueous or acid synthesis of L-ascorbic acid from 2-keto-L-gulonic acid substrates. In an embodiment, product solutions with reduced color are quite evident for reactions run in the presence of sulfite as compared to the absence of sulfite. Reduced color can be deduced by measurement of absorbance of L-ascorbic acid streams containing sulfites versus those not containing sulfites. Generally, sulfites comprise $SO_2$, $HSO_3^-$, $SO_3^{2-}$, $S_2O_3^{2-}$, $S_2O_4^{2-}$, and $S_2O_5^{2-}$, with sulfurous acid being a preferred source of sulfite. Sulfites have been postulated as a means of inhibiting the browning reaction of glucose and amino acids (Wedzicha, B. L., et al., *Adv. In Experimental Medicine and Biology* 289, pp. 217–236, 1991). For example, studies of the Maillard reaction of amino acids has been studied with sulfites (Wedzicha, B. L., *Spec. Publ.—R. Soc. Chem.*, 151, pp. 82–87, 1994). Still, the use of sulfites as a decolorization method or by-product scavenger in ascorbic acid processes derived from 2-keto-1-gulonic acid, its methyl ester, or the bisacetonide of 2-keto-L-gulonic acid has never been described.

In an embodiment, sulfites are employed during the cyclization process (defined herein as in situ). Adding sulfites in situ enables the sulfites to react with by-products as they are being formed, thus reducing subsequent build-up of high molecular weight coloring compounds which eventually precipitate from the reaction. By reducing the formation of these high molecular weight compounds, the sulfite acts to increase the yield of L-ascorbic acid formed. In addition, purification of L-ascorbic acid is optimized as the solid matrix load required for decolorization of the product stream is significantly reduced.

In an embodiment, ascorbic acid is converted from an aqueous solution of 2-keto-L-gulonic acid under conditions that achieve partial conversion. Without being bound by any particular theory, conditions of partial conversion allows for a higher production of ascorbic acid under the reaction conditions. Preferably, the conversion of 2-keto-L-gulonic acid (KLG) or derivatives thereof to L-ascorbic acid is about 5 to 95 percent, more preferably 20 to 75 percent, and even more preferably, 30 to 60 percent.

Thus, the method may comprise batch reactions or continuous reactor format. Referring now to FIG. 1, in an embodiment, the present invention relates to a process for producing L-ascorbic acid (AsA) which comprises the steps of subjecting an aqueous solution of 2-keto-L-gulonic acid (KLG) or derivatives of 2-keto-L-gulonic acid 10 to an acid catalyzed cyclization or a thermal self-catalyzed cyclization 20; removing a post-reaction solution comprising sulfite compounds, unreacted 2-keto-gulonic acid compound and L-ascorbic acid 30; removing the sulfite 35; and separating the product L-ascorbic acid from any unreacted KLG 40. By separating the L-ascorbic acid from the reaction prior to complete conversion of KLG, decomposition of the L-ascorbic acid is minimized. The product stream of L-ascorbic acid 50 from the separation step 40 can then be processed by crystallization 70 or other methods to isolate L-ascorbic acid in its solid form 80. The unreacted KLG separated from the L-ascorbic acid product may be discarded or, in an alternate embodiment, recycled back to the reactor to be further used for production of more L-ascorbic acid.

In an embodiment, the sulfite species may comprise a catalyst for the conversion of 2-keto-L-gulonic acid to L-ascorbic acid. For example, the sulfite may be sulfurous acid. In an embodiment, additional catalysts are added to the reaction. In an embodiment, the catalyst comprises a mineral acid. In an embodiment, the catalyst is HCl, HBr, $H_3PO_4$, or $H_2SO_4$. Alternatively, the reaction may be conducted in the absence of a catalyst, "self-catalyzed" as referred to herein.

In yet another embodiment, the conversion is carried out in the presence of a strongly acidic resin catalyst. Preferably, the catalyst comprises a sulfonated polystyrene cation exchange resin. For example, strongly acidic resin, such as Amberlyst® 15, Amberlyst® 19, Amberlyst® 35 (manufactured by Rohm and Haas Company, Philadelphia, Pa.), Dowex® M-31 or Dowex® G-26 (manufactured by The Dow Chemical Company, Midland, Mich.) may be utilized.

The source of the 2-keto-L-gulonic acid is unimportant in the process of the present invention. Alternative processes for producing 2-keto-L-gulonic acid from glucose (S. Anderson, et. al., *Science*, 230, 144–149, 1985) or sorbose (Y. Saito, *Biotechnol. Bioeng.*, 58 (2 & 3), 309–315, 1998) have been, and continue to be, developed. In an embodiment, the aqueous solution of 2-keto-L-gulonic acid (KLG) is a product stream from a fermentation process for producing KLG. Preferably, an initial purification of this filtrate, such as electrodialysis, ion exchange, or crystallization is undertaken, but is not a precondition for the operation this invention. Alternatively, the 2-keto-L-gulonic acid compound may comprise the hydrolysis products of bisacetonide of 2-keto-L-gulonic acid or the esters of 2-keto-gulonic acid. Regardless of the source of the 2-keto-L-gulonic acid compound, it is preferred that the concentration of 2-keto-L-gulonic acid starting material is about 1 to 40 weight percent, more preferably about 5 to 30 weight percent, and most preferably 8 to 15 weight percent.

The reactions are normally carried out in a solvent. The choice of solvent may be chosen from a wide variety of organic solvents or even water and is only limited by the solubility of the 2-keto-L-gulonic acid and its derivatives and the L-ascorbic acid product in the solvent. Since the 2-keto-L-gulonic acid and its derivatives have limited solubility in non-polar solvents, the preferred solvents would be at least moderately polar. For example, the synthesis of ascorbic acid from 2-keto-L-gulonic acid may utilize an aqueous solvent. As defined herein, "polar" or "moderately polar" comprises molecules which have entities which are positively and/or negatively charged to at least some extent. In an embodiment, the solvent is water. In another embodiment, and especially where esters of 2-keto-L-gulonic are used, the solvent comprises the alcohol corresponding to the alkoxy moiety of the 2-keto-L-gulonic acid ester. Thus, in an embodiment the solvent is methanol. In another embodiment, the solvent is ethanol.

The present invention also describes the use of a continuous process for the generation of L-ascorbic acid. Thus, in one aspect, the present invention comprises a continuous process for manufacturing L-ascorbic acid comprising the steps of: (a) heating an aqueous solution of starting material comprising 2-keto-L-gulonic acid or a derivative thereof in a reactor in the presence of at least one sulfite species under conditions such that L-ascorbic acid is generated; (b) continuously removing from the reactor a post-reaction solution comprising unreacted 2-keto-L-gulonic acid compound and L-ascorbic acid; (c) removing at least a portion of sulfur containing compounds from the post-reaction solution; (d) removing at least a portion of the L-ascorbic acid from the post reaction solution; and (e) recycling unreacted 2-keto-L-gulonic acid compound back to the reactor.

In an embodiment, ion exchange may be used to remove sulfur containing compounds which may include residual sulfite, sulfite by-products and any residual acid by-products. The formation of residual acid by-products includes other poly-acid compounds as well as sulfur containing compounds. Oxidation of sulfite species or sulfur compounds can occur under the conditions used for ascorbic acid synthesis and result in the formation of sulfate species or sulfuric acid. These sulfur containing compounds are collectively removed together by ion exchange. In another embodiment, chromatography, such as simulated moving bed (SMB) chromatography is used for removal of sulfur containing compounds such as sulfites and sulfates. Removal of the sulfur containing compounds may be separate from separation of ascorbic acid and 2-keto-L-gulonic acid, or in an alternate embodiment, simultaneous with separation of ascorbic acid and 2-keto-L-gulonic acid.

In an embodiment, step (d) comprises continuously separating L-ascorbic acid from unreacted 2-keto-L-gulonic acid in the post reaction solution to form an L-ascorbic acid rich solution and a crude 2-keto-L-gulonic acid solution. Thus, the present invention teaches the operation of a separation process prior to ascorbic acid recovery. This separation improves overall reaction efficiency by providing for unreacted 2-keto-L-gulonic acid to be recycled back to the reactor, and thereby enhances the overall yield of ascorbic acid. Operation of a continuous reaction system with partial conversion of 2-keto-L-gulonic acid and a recycle step dramatically improves the overall yield to ascorbic acid. Because ascorbic acid is unstable for long periods of time under the reaction conditions (e.g. P. P. Regna and B. P. Caldwell, *J. Am. Chem. Soc.*, 66, pp. 246–250, 1944), ascorbic acid yields in a single pass process are limited by the selectivity for ascorbic acid in the reactor, which decreases with increasing 2-keto-L-gulonic acid conversion, since conditions that lead to high conversion promote decomposition of the product.

Common separation techniques contemplated for separation of 2-keto-L-gulonic acid and L-ascorbic acid through the practice of the invention include fractional crystallization, electrodialysis membrane separation, and chromatographic methods. Fractional crystallization, however, is generally an inefficient means of recovering ascorbic acid directly from a process stream containing a significant amount of 2-keto-L-gulonic acid (KLG) unless combined with other separation techniques (see e.g. U.S. Pat. No. 5,817,238).

Electrodialysis separation operates on the principle that acids with differing pKa's migrate at different rates through a cell containing a membrane so that the more dissociated species will migrate first or preferentially. Electrodialysis membranes operated with anion exchange resins can separate L-ascorbic acid from other components with differing pKa's (see e.g. U.S. Pat. No. 6,004,445; EP 0 554090 A2). Operating the electrodialysis separation on a stream of 2-keto-L-gulonic acid and L-ascorbic acid would allow the 2-keto-L-gulonic acid to be recycled back to the conversion step and the L-ascorbic acid to be recovered in a subsequent step.

Chromatographic separation may employ, for example, acid retardation based ion exclusion. Ion exclusion separation occurs when acids of different dissociation constants (pKa) are brought in contact with a cation exchange resin. The negative charge on the cation exchange resin repels the negatively charged anions formed by the dissociation of the acids. The stronger acid (i.e. more dissociated) is excluded from the resin structure to a greater extent than a weaker acid. For example, in WO 97/13761, a process is described for recovering L-ascorbic acid by adsorption of L-ascorbic acid on to a resin. The L-ascorbic acid is then desorbed with a neutral solvent such that the concentration of the L-ascorbic acid in the eluant is at least as concentrated as the L-ascorbic acid in the aqueous feed stream.

In an embodiment, the separation process of step (d), or steps (c) and (d) together, comprise SMB chromatography. For example, U.S. Pat. No. 5,817,238, incorporated herein by reference, describes the use of SMB chromatography for recovery of L-ascorbic acid from a mother liquor obtained during crystallization of L-ascorbic acid. The purified L-ascorbic acid is then recycled back into the crystallization process for further purification. In the separation process described in U.S. Pat. No. 5,817,238, however, the 2-keto-L-gulonic acid concentration is sufficiently dilute (<5% w/v) such that there is no attempt to recover the 2-keto-L-gulonic acid or to recycle it for further production of L-ascorbic acid.

Thus, while other chromatographic methods such as elution chromatography may be employed, simulated moving bed (SMB) chromatography is generally more efficient for a large scale process in that it provides greater separation per volume of adsorbant. In the SMB process, the feed, desorbant, and product ports are moved intermittently in the direction of fluid flow. This simulates the counter-current movement of the resin (see e.g., Wankat, P. C., *Rate-Controlled Separations*, Elsevier Applied Science, N.Y., 1990, pp. 524–541). The SMB process is typically operated to accomplish a binary separation. This is the embodiment shown in FIG. 2. However, modified SMB processes can be employed to accomplish ternary separations. One approach is to use two SMB units in series. The first SMB would split the ternary mix containing components A, B, and C, into a stream containing pure C and a stream containing a mixture of A and B. The second SMB would then split A and B into two streams containing pure A and pure B.

Alternatively, a single SMB can be operated such that a pure C stream (stream 1), a stream containing B with a significant amount of A (stream 2), and a stream containing pure A (stream 3) are obtained (Navarro, A., et al., *J. of Chromatography A*, 1997, 770, pp. 39–50). Component C will be recovered at a high rate in stream 1 and component B will be recovered at a high rate in stream 2. For example, and referring now to FIG. 3, in the synthesis of L-ascorbic acid from 2-keto-L-gulonic acid, a reactor effluent will contain L-ascorbic acid, 2-keto-L-gulonic acid, and sulfur species.

In an embodiment, a SMB unit is comprised of either a single multi-section column or a series of columns with solenoid valves. In both cases, the column or columns are packed with resin and fed both a solution to be separated and a displacer (usually water) via two different ports. Resins suitable for SMB include Dowex Monosphere 99H (The Dow Chemical Co., Midland, Mich.), Amberlite CR1320 H (The Rohm and Haas Co., Philidelphia Pa.) and Purolite 642 H (Philadelphia, Pa.). Generally, water is used as the desorbant. Other solvents, however, are within the scope of the present invention. The ratio of desorbant:feed (vol/vol) will depend on the parameters of the system.

Figure 2:
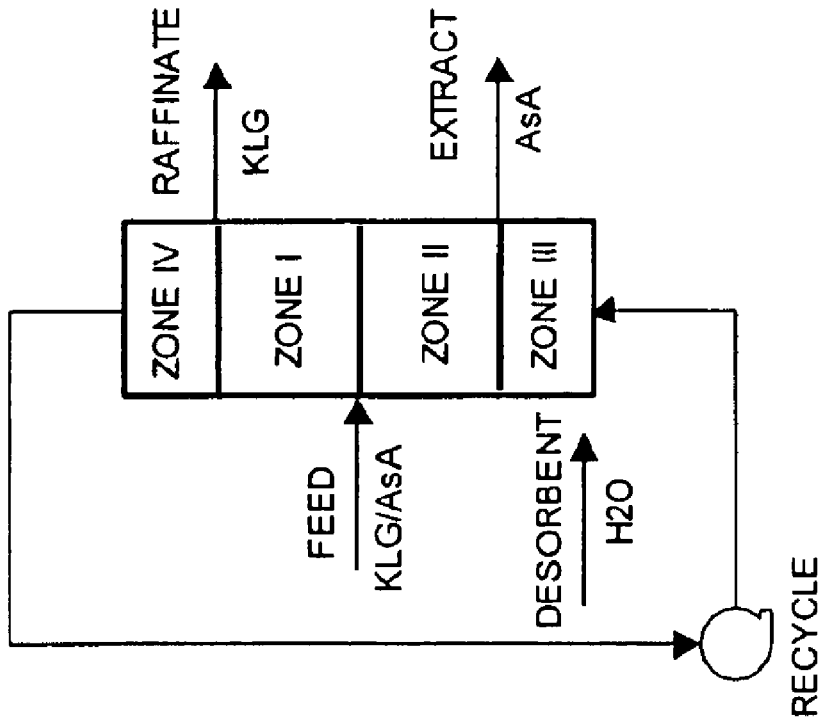
FIG. 2 is a schematic representation of simulated moving bed chromatographic purification of L-ascorbic acid product (AsA) from raffinate comprising 2-keto-L-gulonic acid (KLG) in accordance with an embodiment of the present invention.

The SMB unit may be operated at room temperature, and is limited at the lower end by the temperature at which the solutions become saturated and at the upper end by the stability of the resin at high temperatures. Thus, suitable temperatures may comprise 20 to 100° C., and more preferably 20 to 70° C. Because the column is also fed a displacer (which moves in conjunction with the feed and outlet ports and serves as a regenerant), the product streams will be diluted with the displacer. Typically, the displacer is the same solvent as the feed solvent. The intermittent port movement in the direction of liquid flow simulates the counter-current movement of the resin bed. Thus, as depicted in FIG. 2, the resin is moving faster than the ascorbic acid, but slower than the KLG.

Figure 3:
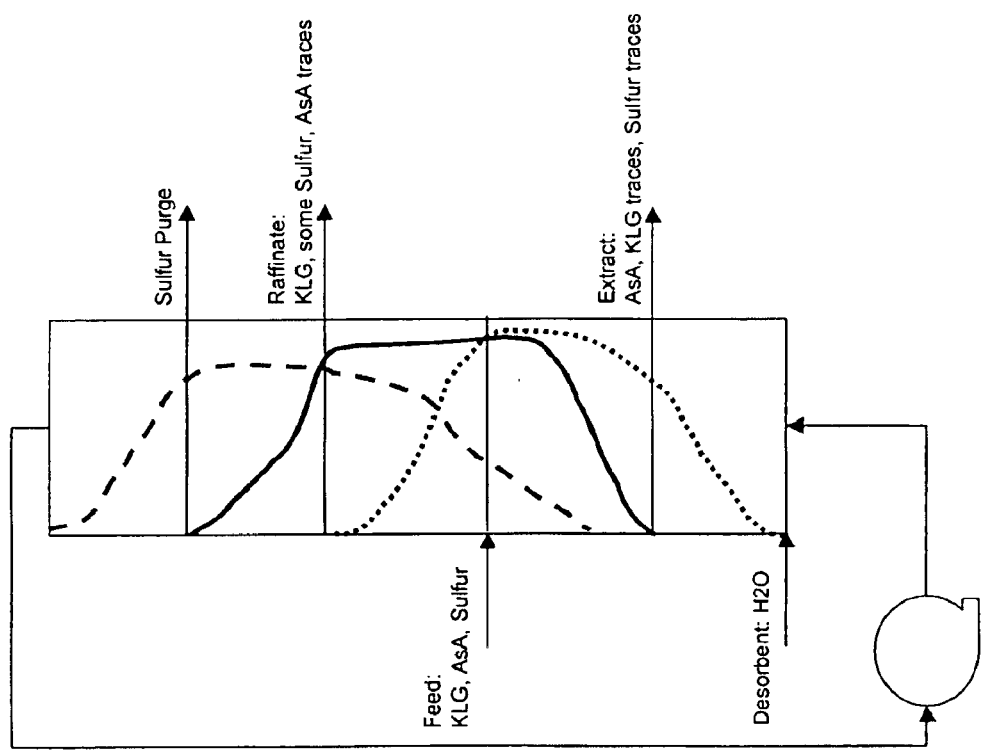
FIG. 3 is a schematic representation of a 5-zone simulated moving bed chromatographic purification of L-ascorbic acid product (AsA), 2-keto-L-gulonic acid (KLG), and sulfur (sulfite) compounds in accordance with an embodiment of the present invention.

In an embodiment, 5-zone SMB chromatography is used for the simultaneous purification of L-ascorbic acid, unreacted 2-keto-L-gulonic acid, and sulfite complexes. Thus, using 5-zone SMB chromatography, three streams are obtained: an almost pure ascorbic acid stream, a stream containing 2-keto-L-gulonic acid and significant amounts of sulfur compounds, and a stream containing sulfur compounds (FIGS. 3 and 4).

Figure 4:
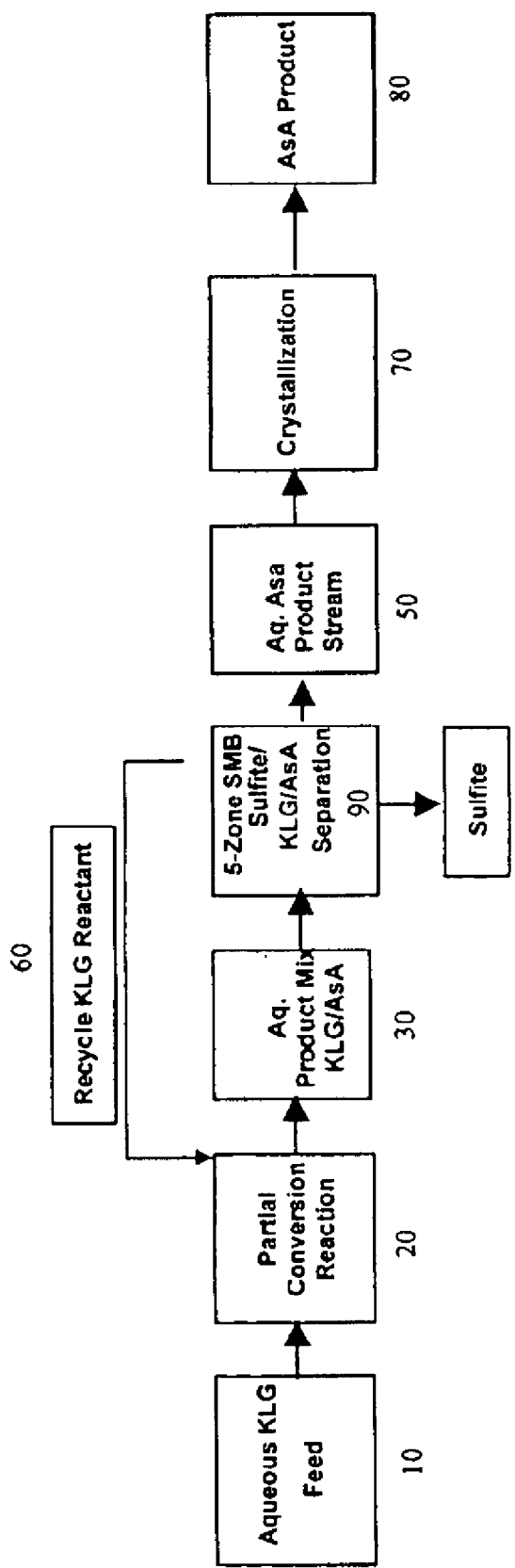
FIG. 4 is a schematic representation of the overall process for L-ascorbic acid synthesis comprising 5-zone SMB chromatographic purification of sulfur containing compounds (e.g. sulfites), 2-keto-L-gulonic acid (KLG) which is then recycled back to the reaction, and L-ascorbic acid (AsA) which is further purified by crystallization in accordance with an embodiment of the present invention.

As shown in FIG. 4, in an embodiment, the pure ascorbic acid stream 50 is taken to the next step for crystallization 70 and product isolation 80, the 2-keto-L-gulonic acid stream 60 is recycled back to the reactor, and the sulfur stream comprising sulfites and sulfite-bound high molecular weight discoloration products 35 is discarded. Thus, the stream containing sulfur compounds is a convenient way to purge a substantial portion of the sulfur containing compounds.

Figure 5:
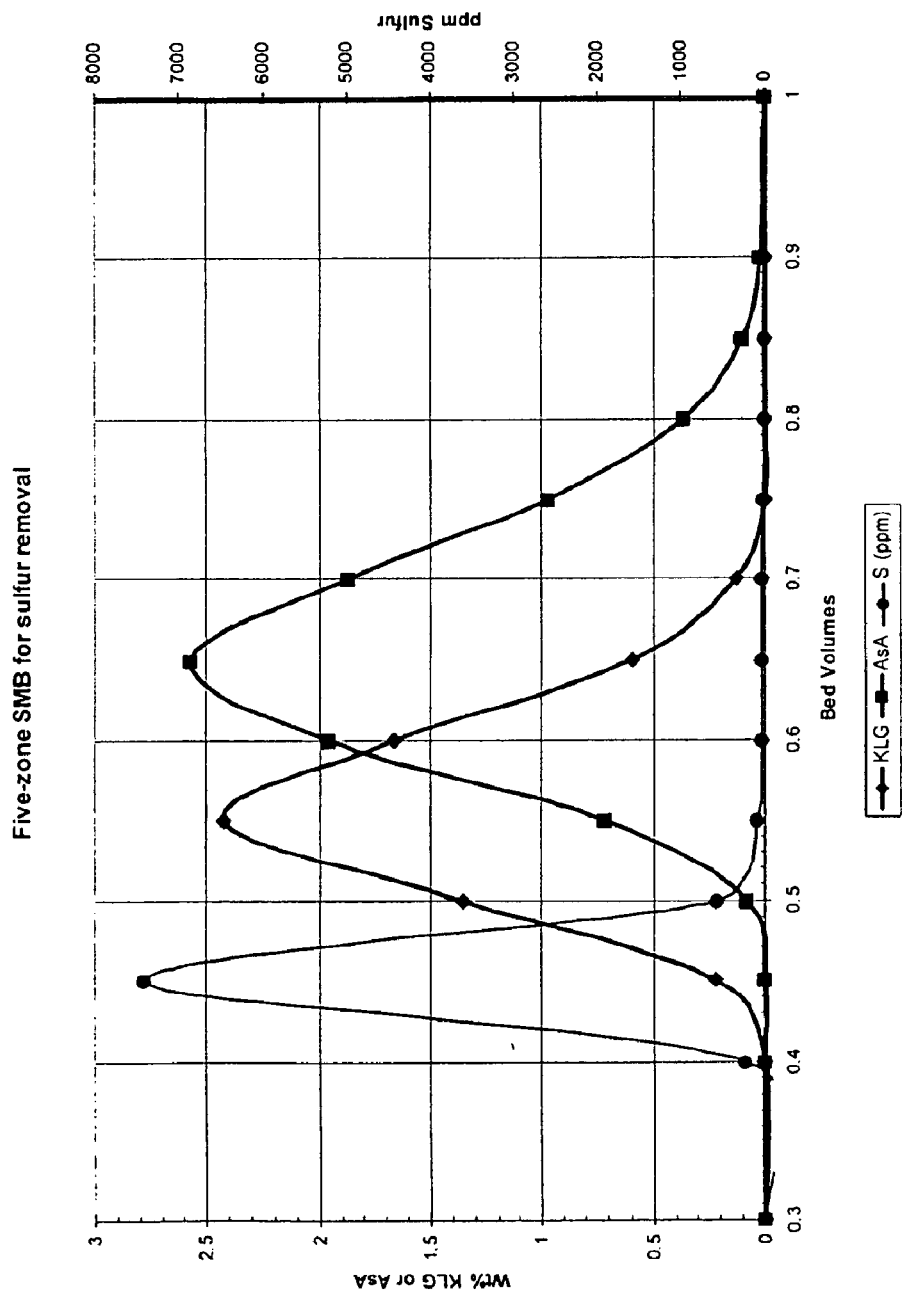
FIG. 5 shows a pulse test separation of sulfurous acid (S), 2-keto-L-gulonic acid (KLG), and L-ascorbic acid (AsA) using ion exclusion chromatography in accordance with an embodiment of the present invention.

Referring now to FIG. 5, a pulse test by ion exclusion chromatography was conducted using as feed a reactor effluent containing ascorbic acid, 2-keto-L-gulonic acid, and sulfur compounds. Thus, in an embodiment, there is a clear peak-to-peak separation between ascorbic acid and 2-keto-L-gulonic acid and between 2-keto-L-gulonic acid and sulfur compounds.

Figure 6:
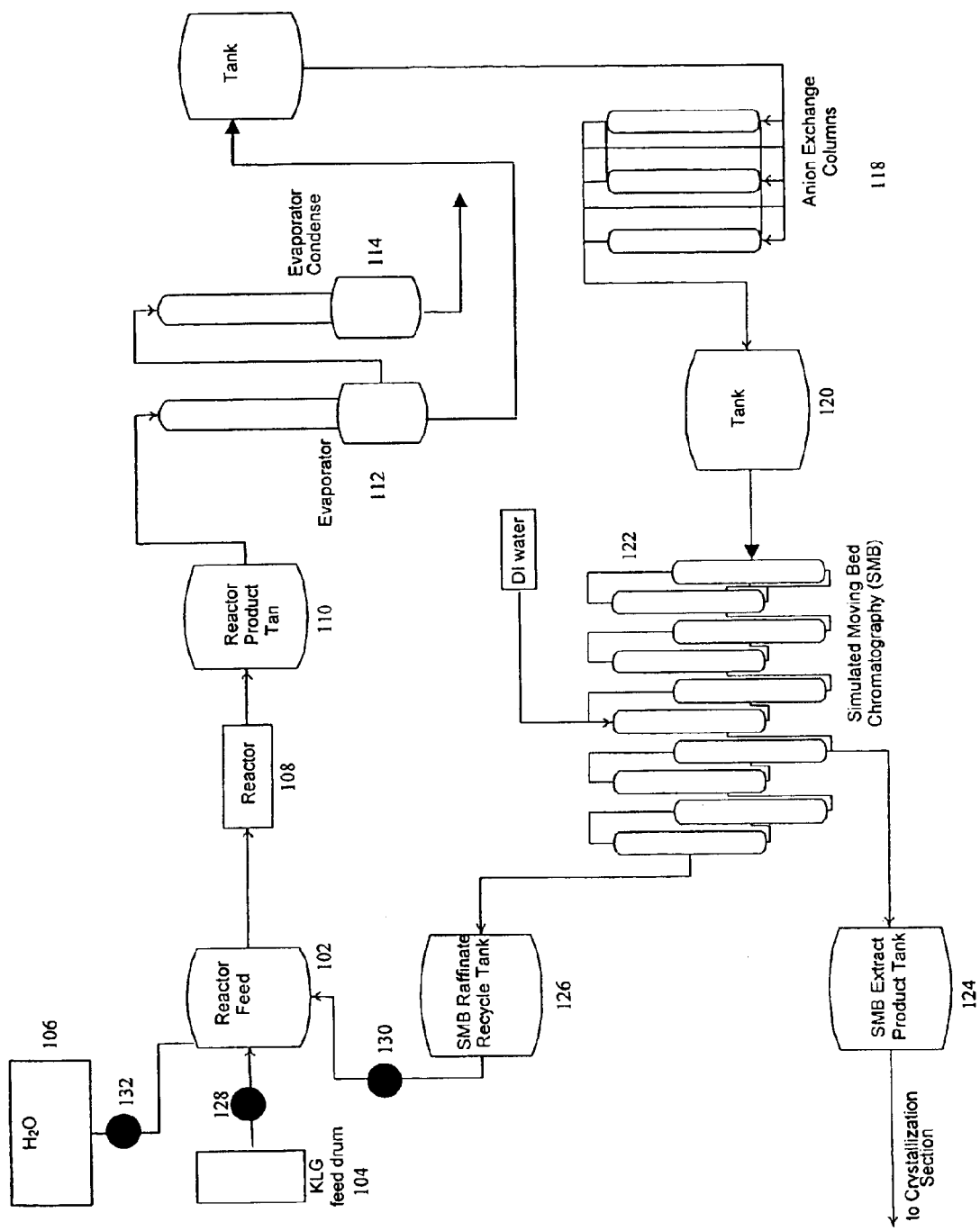
FIG. 6 shows a schematic representation of a reactor used in pilot experiments in accordance with an embodiment of the present invention.

FIG. 6 shows a system for generation of L-ascorbic acid by partial conversion and recycle of 2-keto-L-gulonic acid (KLG) in accordance with an embodiment of the present invention. Thus, the system may comprise a continuous reactor 108 which may be submerged in a silicone oil bath heated to the desired reaction temperature. Feeding into reactor 108 is tank 102 comprising reactor feed. The reactor feed is in turn comprised of fresh KLG (e.g. purified fermentation broth stored in feed drum) and, in a preferred embodiment, recycled KLG (stored as SMB raffinate recycle) isolated from reactor product.

In an embodiment, the system comprises a simulated moving bed (SMB) chromatographic system 122 for separation of L-ascorbic acid and 2-KLG. The SMB unit may comprise multiple columns packed with resin such as monodisperse cation exchange resins such as Dowex Monospere 99 H, A-561 (The Dow Chemical Co., Midland, Mich.), Amberlite CR1320 H (The Rohm and Haas Co., Philidelphia Pa.) and Purolite 642 H (Philadelphia, Pa.). Generally, water is used as the desorbant. Other solvents, however, are within the scope of the present invention.

The system may comprise tanks for transient storage of starting materials, reaction intermediates, and reaction products. In an embodiment, tank 104 comprises a drum for fresh (i.e. non-recycled) KLG, tank 106 comprises a tank holding water, and tank 126 comprises a tank for KLG recycled from the SMB unit and prior reactions. Movement of fluid into, and out of, the tanks may be regulated to have a continuous mass balance throughout the system. For example, pumps 128, 130, and 132 may used to control fluid flow into reactor tank 102, whereas other pumps may be used to control fluid flow throughout other parts of the system.

Generally, components are sized for maximal efficiency in handling the volume of materials cycled through the system. Thus, in an embodiment, the system comprises additional units to improve the control of fluid flow throughout the system. For example, the system may comprise an evaporator system 112, 114, which reduces the volume of material going into the separation system. The system may also include an anionic exchange system 118 for removal of sulfur containing compounds prior to SMB separation.

In a preferred embodiment, L-ascorbic acid purified by SMB is stored in SMB product tank 124 prior to further purification. Purification of the L-ascorbic acid from the SMB purified product generally comprises crystallization, although other techniques known in the art may be used as well.

In yet another embodiment, the present invention comprises contacting an aqueous solution of L-ascorbic acid product, or 2-keto-L-gulonic acid and ascorbic acid (i.e. a post-reaction solution from a partial conversion reaction) with sulfites after completion of the cyclization reaction. Addition of sulfite to the L-ascorbic acid product helps to decolor the product by complexing or partially reacting with colorization products, such as colored or unsaturated byproducts, present in the product stream. In this embodiment, the present invention comprises a process operated in such a way as to maximize production of ascorbic acid in the separation step or a recovery process followed by a subsequent treatment of the ascorbic acid stream with sulfites. The separation process for ascorbic acid and sulfite species may be operated in such a way that an efficient separation process would allow the majority of the sulfite species to be removed, as described above. The product stream containing ascorbic acid from the separation process can then be subjected to subsequent adsorption based decolorization or carbon treatment followed by recovery to obtain crystalline ascorbic acid product.

EXAMPLES

The present invention may be further understood by reference to the following non-limiting examples. As used herein, percent conversion (of 2-keto-L-gulonic acid to L-ascorbic acid) and percent selectivity of the reaction are defined as described below.

$$KLG\_Conversion, \% = 100\% \times \left(1 - \frac{x_{KLG}^{Product}}{x_{KLG}^{Feed}}\right)$$

$$AsA\_Selectivity, mol \% = 100\% \times \left(\frac{194.15 \times (x_{AsA}^{Product} - x_{AsA}^{Feed})}{176.13 \times (x_{KLG}^{Feed} - x_{KLG}^{Product})}\right)$$

where $x_i^j$ is the composition by weight of KLG or AsA (i) in the reactor feed or product (j).

Examples 1–3

Examples 1–3 (Table 1) illustrate the effect of bisulfite additive concentration on the percent conversion of 2-keto-L-gulonic acid to ascorbic acid and the selectivity of the reaction. In example 1, four samples each of a 10 wt % solution of 2-keto-L-gulonic acid (anhydride basis) without any sulfite were heated for 2 hours at 120° C., cooled in an ice bath, then assayed by high performance liquid chromatography (HPLC) for 2-keto-L-gulonic acid and ascorbic acid. In examples 2 and 3, four samples each of a 10 wt % solution of 2-keto-L-gulonic acid (anhydride basis) with 0.07 wt % sodium bisulfite ($NaHSO_3$) or 0.13 wt % sodium bisulfite ($NaHSO_3$), respectively, were treated as described for example 1. The average percent conversion of 2-keto-L-gulonic acid and percent selectivity to ascorbic acid of the four samples used in each example was calculated and is presented in Table 1.

It can be seen that increasing sulfite does not reduce, and may actually enhance selectivity.

TABLE 1

| Example Number | Sodium Bisulfite (wt %) | Average Conversion (%) | Average Selectivity (%) |
|---|---|---|---|
| 1 | 0 | 47.57 | 80.24 |
| 2 | 0.07 | 49.30 | 86.03 |
| 3 | 0.13 | 46.52 | 86.50 |

Examples 4–8

Figure 7:
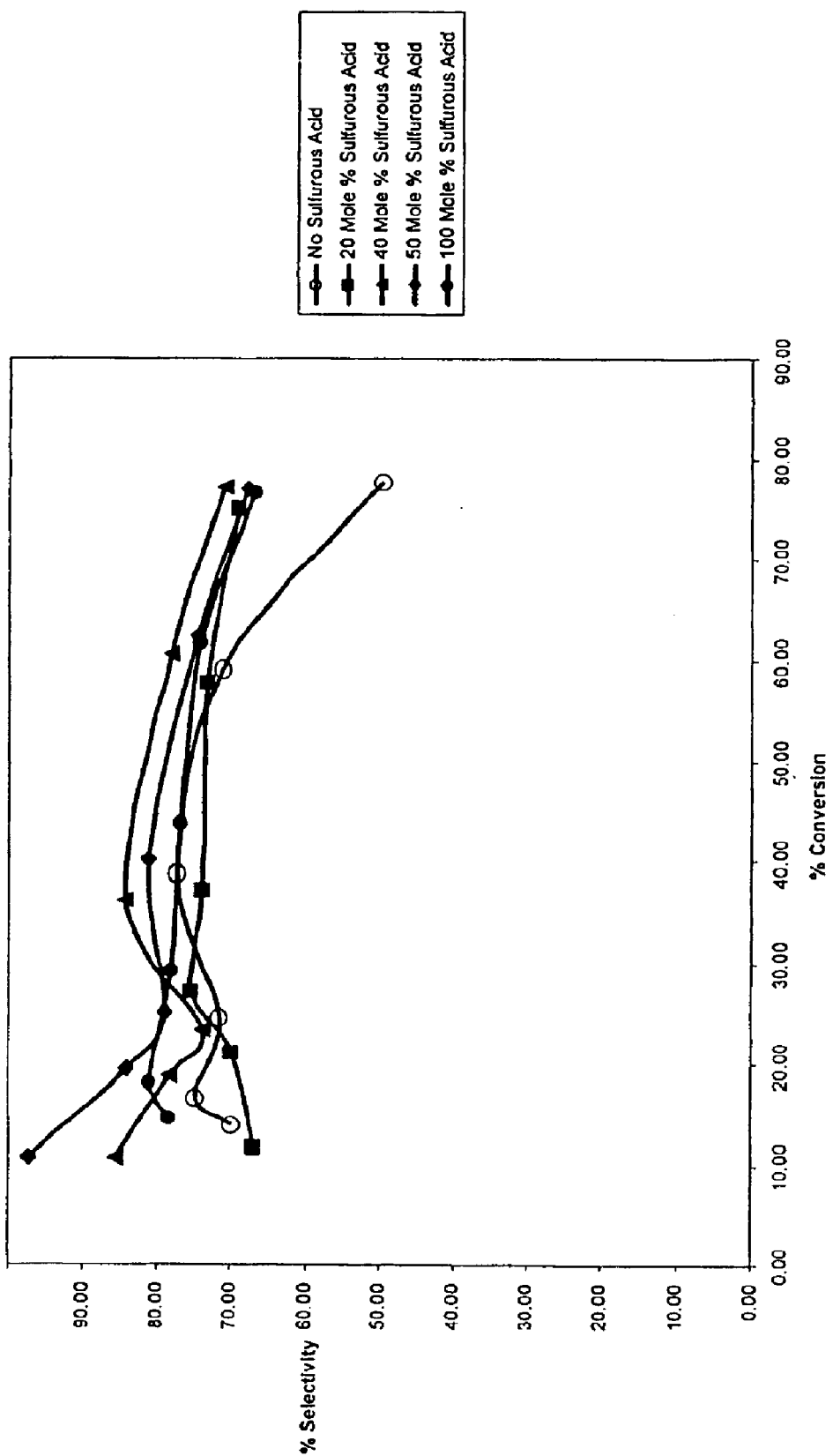
FIG. 7 shows the effect of addition of increasing amounts of sulfurous acid to batch reaction synthesis of L-ascorbic acid from 2-keto-L-gulonic acid in accordance with an embodiment of the present invention.

Examples 4–8 illustrate the effect of sulfurous acid as an additive on reaction selectivity. These reactions were carried out in a series of batch reaction vials at partial conversion. The data is summarized in Table 2, and a plot of percent selectivity versus percent conversion is shown in FIG. 7.

In examples 4–8, a series of six 2.5 mL samples each containing a 10 wt % solution of 2-keto-L-gulonic acid (anhydride basis) were heated at 115° C. in the presence of 0, 20, 40, 50, and 100 mole % (relative to the amount of 2-keto-L-gulonic acid) sulfuric acid for a given time period as indicated in Table 2. Subsequently, the samples were cooled in an ice bath and assayed by HPLC for 2-keto-L-gulonic acid and ascorbic acid. The percent conversion of 2-keto-L-gulonic acid and percent selectivity to ascorbic acid at each time is presented in Table 2. As noted for Examples 1–3, addition of sulfuric acid was found to enhance selectivity in some cases.

TABLE 2

| | | | Product HPLC Results | | | |
|---|---|---|---|---|---|---|
| Example | Time, minutes | Mole % Sulfurous acid | KLG (Anh), Wt % | AsA, Wt % | Conversion, mole % | Selectivity, mole % |
| 4.0 | 0 | 0 | 10.15 | 0.12 | 0.00 | 100.00 |
| 4.1 | 5 | 0 | 8.73 | 1.02 | 13.99 | 69.88 |
| 4.2 | 15 | 0 | 8.45 | 1.27 | 16.75 | 74.58 |
| 4.3 | 30 | 0 | 7.65 | 1.74 | 24.63 | 71.44 |
| 4.4 | 60 | 0 | 6.2 | 2.89 | 38.92 | 77.32 |
| 4.5 | 120 | 0 | 4.14 | 4 | 59.21 | 71.18 |

TABLE 2-continued

Product HPLC Results

| Example | Time, minutes | Mole % Sulfurous acid | KLG (Anh), Wt % | AsA, Wt % | Conversion, mole % | Selectivity, mole % |
|---|---|---|---|---|---|---|
| 4.6 | 180 | 0 | 2.24 | 3.68 | 77.93 | 49.62 |
| 5.0 | 0 | 20 | 9.96 | 0.13 | 0.00 | 100.00 |
| 5.1 | 5 | 20 | 8.79 | 0.84 | 11.75 | 66.91 |
| 5.2 | 15 | 20 | 7.86 | 1.46 | 21.08 | 69.83 |
| 5.3 | 30 | 20 | 7.24 | 1.99 | 27.31 | 75.39 |
| 5.4 | 60 | 20 | 6.23 | 2.63 | 37.45 | 73.90 |
| 5.5 | 120 | 20 | 4.19 | 3.96 | 57.93 | 73.18 |
| 5.6 | 180 | 20 | 2.47 | 4.82 | 75.20 | 69.04 |
| 6.0 | 0 | 40 | 8.8 | 0.11 | 0.00 | 100.00 |
| 6.1 | 5 | 40 | 7.86 | 0.84 | 10.68 | 85.62 |
| 6.2 | 15 | 40 | 7.14 | 1.29 | 18.86 | 78.37 |
| 6.3 | 30 | 40 | 6.74 | 1.49 | 23.41 | 73.86 |
| 6.4 | 60 | 40 | 5.6 | 2.56 | 36.36 | 84.41 |
| 6.5 | 120 | 40 | 3.47 | 3.88 | 60.57 | 77.98 |
| 6.6 | 180 | 40 | 2 | 4.48 | 77.27 | 70.85 |
| 7.0 | 0 | 50 | 10.2 | 0.13 | 0.00 | 100.00 |
| 7.1 | 5 | 50 | 9.1 | 1.1 | 10.78 | 97.22 |
| 7.2 | 15 | 50 | 8.21 | 1.65 | 19.51 | 84.21 |
| 7.3 | 30 | 50 | 7.63 | 1.97 | 25.20 | 78.94 |
| 7.4 | 60 | 50 | 6.11 | 3.14 | 40.10 | 81.14 |
| 7.5 | 120 | 50 | 3.84 | 4.42 | 62.35 | 74.37 |
| 7.6 | 180 | 50 | 2.33 | 4.97 | 77.16 | 67.81 |
| 8.0 | 0 | 100 | 10.32 | 0.13 | 0.00 | 100.00 |
| 8.1 | 5 | 100 | 8.8 | 1.21 | 14.73 | 78.34 |
| 8.2 | 15 | 100 | 8.44 | 1.51 | 18.22 | 80.93 |
| 8.3 | 30 | 100 | 7.28 | 2.28 | 29.46 | 77.98 |
| 8.4 | 60 | 100 | 5.78 | 3.29 | 43.99 | 76.74 |
| 8.5 | 120 | 100 | 3.95 | 4.41 | 61.72 | 74.08 |
| 8.6 | 180 | 100 | 2.4 | 4.92 | 76.74 | 66.68 |

TABLE 3

| Example | Contact Time (min) | Temperature (deg. C.) | KLG Concentration (wt %) | $H_2SO_3$ mole % relative to KLG | Conversion | Selectivity | Absorbance (Absolute increase) | Absorbance (% Increase) |
|---|---|---|---|---|---|---|---|---|
| 9 | 7.5 | 120 | 5 | 0 | 42.81 | 77.85 | 0.1392 | 93.2 |
| 10 | 7.5 | 120 | 5 | 30 | 48.57 | 85.61 | 0.0346 | 76.1 |
| 11 | 7.5 | 120 | 10 | 15 | 53.73 | 76.3 | 0.1752 | 88.1 |
| 12 | 7.5 | 120 | 15 | 0 | 55.05 | 71.07 | 0.0791 | 95 . |
| 13 | 7.5 | 120 | 15 | 30 | 61.83 | 73.58 | 0.3878 | 92 . |
| 14 | 3.5 | 150 | 5 | 15 | 36.65 | 84.23 | 0.0235 | 69 . |
| 15 | 3.5 | 150 | 10 | 0 | 41.72 | 78.26 | 0.2192 | 89.9 |
| 16 | 3.5 | 150 | 10 | 15 | 45.62 | 79.37 | 0.0791 | 77.5 |
| 17 | 3.5 | 150 | 10 | 30 | 46.25 | 82 . | 0.0660 | 75.5 |
| 18 | 3.5 | 150 | 15 | 15 | 46.3 | 75.23 | 0.1584 | 81.1 |
| 19 | 2.3 | 180 | 5 | 0 | 39.56 | 83.73 | 0.1075 | 91.9 |
| 20 | 2.3 | 180 | 5 | 30 | 51.71 | 80.84 | 0.0324 | 74.6 |
| 21 | 2.3 | 180 | 10 | 15 | 49.04 | 75.87 | 0.1161 | 83.5 |
| 22 | 2.3 | 180 | 15 | 0 | 45.83 | 72.38 | 0.5240 | 93.9 |
| 23 | 2.3 | 180 | 15 | 30 | 47.05 | 73.1 | 0.0607 | 63.7 |

Examples 9–23

Examples 9–23 illustrate the effect of sulfurous acid concentration on the percent selectivity and solution color as a function of conversion of 2-keto-L-gulonic acid to L-ascorbic acid relative to a reference example with no sulfurous acid added. These reactions were carried out with continuous feeds in a ⅛" O.D.×50' long (30 mL volume) Teflon tube reactor at temperatures of 120, 150, and 180° C. with a total pressure of 165 psig. Contact time for the continuous reactor system is equivalent to the reactor volume divided by the volumetric flow rate of the feed and is analogous to reaction time in a batch experiment.

The results are shown in Table 3. The reduced color of solutions treated with sulfurous acid was measured by absorbance at 450 nm. In all cases, an increase in color was observed upon conversion and is represented as an absolute increase in absorbance. The difference in absorbance of feed and product solutions (standardized against the appropriate concentrations of 2-keto-L-gulonic acid and sulfurous acid) is represented by the percent increase in color after reaction by comparing the feed solution to the product solution. It was found that samples not treated with sulfurous acid had a significantly greater absorbance and greater percent increase in color relative to those examples with sulfurous acid.

Example 24

Example 24 illustrates the separation of a solution containing a mixture of sulfurous acid, 2-keto-L-gulonic acid and L-ascorbic acid by ion exclusion in a pulse test. A 0.2 bed volume pulse of a feed mixture consisting of 15% 2-keto-L-gulonic acid, 15% L-ascorbic acid and sulfurous acid (5.4 wt %) was fed to a column packed with an ion exclusion resin. The feed mixture was eluted by water. Referring to FIG. 5, a peak-to-peak separation of sulfur species (S), 2-keto-L-gulonic acid (KLG) and L-ascorbic acid (AsA) is shown. The peak of the sulfur species, 2-keto-L-gulonic acid and L-ascorbic acid are shown to separate by 0.1 bed volumes. This separation in a pulse test is a demonstration of the feasibility of separating sulfur species, 2-keto-L-gulonic acid from L-ascorbic acid in a SMB unit.

Example 25

For this experiment, the system included a continuous reactor, a tank comprising reactor feed, syringe pumps for feeding $SO_2$ into the reactor, a simulated moving bed (SMB) chromatographic system for separation of L-ascorbic acid and unreacted KLG, and anionic exchange columns for purification of sulfite containing compounds from the reaction product. The system also included a system for crystallization of L-ascorbic acid in the SMB extract.

The thermal conversion of 2-keto-L-gulonic acid (KLG) to ascorbic acid (AsA) was performed in 40-feet of coiled ¼-inch OD titanium tubing immersed in a silicone oil (Dow Corning 550) bath. With a wall thickness of 0.035" and heated length of approximately 37 ft, the effective reactor volume was about 185 ml. In these experiments, reactor feed rates ranged from 60 to 80 ml/min with the average of 70 ml/min corresponding to a reactor space-time of 2.6 min. The bath temperature ranged from 172 to 181° C. at the given feed rate. Two heaters were used simultaneously in a 2 ft×2 ft×1 ft (20–25 gals of silicone oil) bath: (1) a 3 kW immersion heater with a variable output set by a powerstat (typically at 50–70%) to provide base load heating and, (2) a 1.2 kW Haake DL30 immersion circulator to control the bath temperature and circulate the oil.

As shown schematically in FIG. 6, the system included tanks (or other storage means) for transient storage of starting materials, reaction intermediates, and reaction products. For example, feeding into the reactor was a tank comprising reactor feed. The reactor feed was in turn comprised of fresh KLG (e.g. purified fermentation broth stored in feed drum), recycled KLG isolated from the SMB purified reactor product, and deionized water for diluting the reactants to appropriate concentrations. Fresh feed from fermentation broth purified by calcium sulfate precipitation and filtration (Genencor, Palo Alto, Calif.). Movement of fluid into, and out of the tanks was regulated to have a continuous mass balance throughout the system. The system also included an evaporator unit which was used to reduce the volume of material going into the separation system and an anionic exchange system for separating out the sulfite material from the post-reaction solution.

Pumps (e.g. FMI Metering Pump; Syosset, N.Y.) were used to pump fluids throughout the system. For example, a pump was used to transfer fresh KLG into the pre-reactor tank, a pump was used to transfer the KLG recycle from the SMB system back into the pre-reactor tank, and another pump was used to transfer deionized water to the pre-reactor tank. The pre-reactor tank was 22-liter glass feed tank, and had two sets of dual ISCO syringe pumps to separately feed either aqueous KLG or other components (e.g. catalysts and/or sulfites) to the reactor.

To maintain liquid-phase conditions throughout, the pressure in the reactor was kept well above the vapor pressure of water at reaction temperature (about 145 psia @ 180° C.) using a Tescom back-pressure regulator. Also, relief valves (250 psig) were included in the system to prevent local over-pressuring in the system. Thus, pressures were bounded by 250-psig relief valves on the KLG feed lines, with a minimum pressure of about 150 psig imposed to keep the reactor contents in the liquid phase.

Sulfur dioxide was fed initially as a pure liquid (0.1–0.25 ml/min) and later as a saturated aqueous solution (sulfurous acid, about 5–9 wt. % $SO_2$; 3.3–4.3 ml/min). In both cases, the $SO_2$ was maintained at about 80 psig with nitrogen to keep it in the liquid phase.

The reactor effluent was cooled in a double-pipe (Ti in Cu) exchanger and then filtered (Pall Profile II cartridges, polypropylene, 2.5" OD×5" L, generally 20 $\mu$m although some 10 $\mu$m cartridges were used) to prevent solid by-products from going downstream and to protect the back-pressure regulator. Initially a single filter housing (Crall Products) and bypass were used, although multiple (at least two) parallel filters were generally preferred.

All heated sections were constructed of titanium or PFA fluoropolymer. Stainless steel valves, piping, and other components were used both before the reactor and after cooling the effluent. Corrosion coupons were placed in the KLG recycle, KLG feed, and reactor product tanks.

Pilot Reactor Operation

The control strategy for the system as a whole centered around adjusting unit feed (or product in the case of the evaporator) rates to match the unit downstream. Because the SMB feed rate was narrowly constrained, its feed and product rates remained relatively constant. Also, the controlled rates for the evaporator, and SMB were based on concentrated material (>35% solids) while reactor feeds and products were dilute (<15% solids). Thus, the reactor, as the unit furthest away from the SMB feed, required the largest and most frequent rate changes.

It was found that there is a approximately linear relationship between feed rate of the KLG and the temperature required to maintain the appropriate conversion level. Thus, for a feed rate ranging from about 45 to 95 ml/min, a KLG conversion of 60% required temperatures ranging from about 170 to 185° C. At the same feed rate, the temperature needed for 50% conversion was about 5–6° C. lower. Thus, based on the feed rate for the KLG, the temperature could be adjusted to maintain the appropriate conversion level.

It was found that, in some cases, the use of pure $SO_2$ could result in the formation of solid deposits. Switching from pure to aqueous $SO_2$ significantly reduced the formation of deposits (and associated localized pressure spikes). In addition, solid by-products which can form upon cooling the post reaction solution from the conversion of KLG to L-ascorbic acid were filtered from the post-reaction solution prior to separation and purification of the KLG and AsA from the post-reaction solution.

Pilot Reactor Performance

Figure 8:
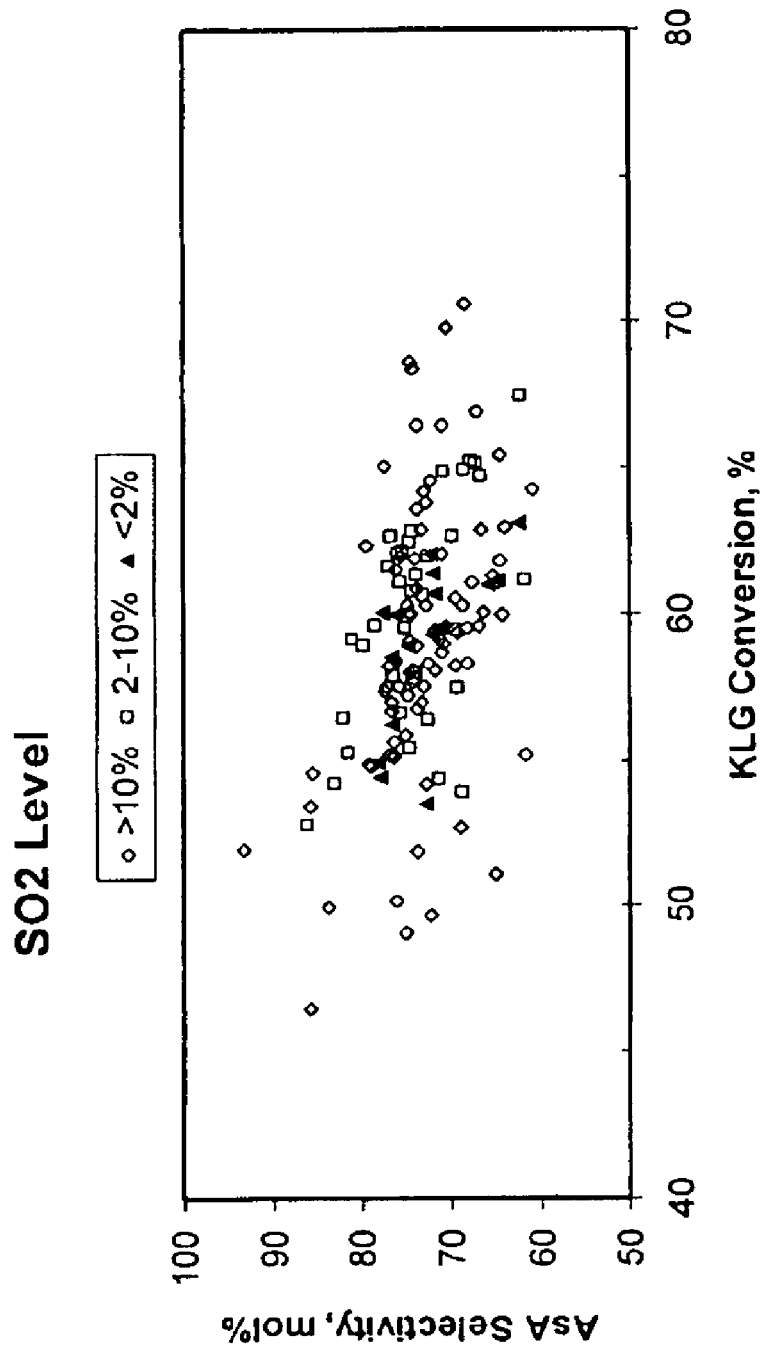
FIG. 8 shows L-ascorbic acid (AsA) selectivity for a continuous reactor at various 2-keto-L-gulonic acid (KLG) conversion levels in the presence of different amounts of sulfite in accordance with an embodiment of the present invention.

The key measures of reactor performance are KLG conversion, selectivity to AsA. Other than brief periods at the beginning and end of the run, KLG conversion was generally maintained at 55–65%. Selectivity to AsA was generally 65–80 mole % with no obvious dependence of the $SO_2$ feed level (FIG. 8). In addition, it was found that selectivity was essentially independent of the feed concentration of KLG over the range (8–11% KLG) employed.

Figure 9:
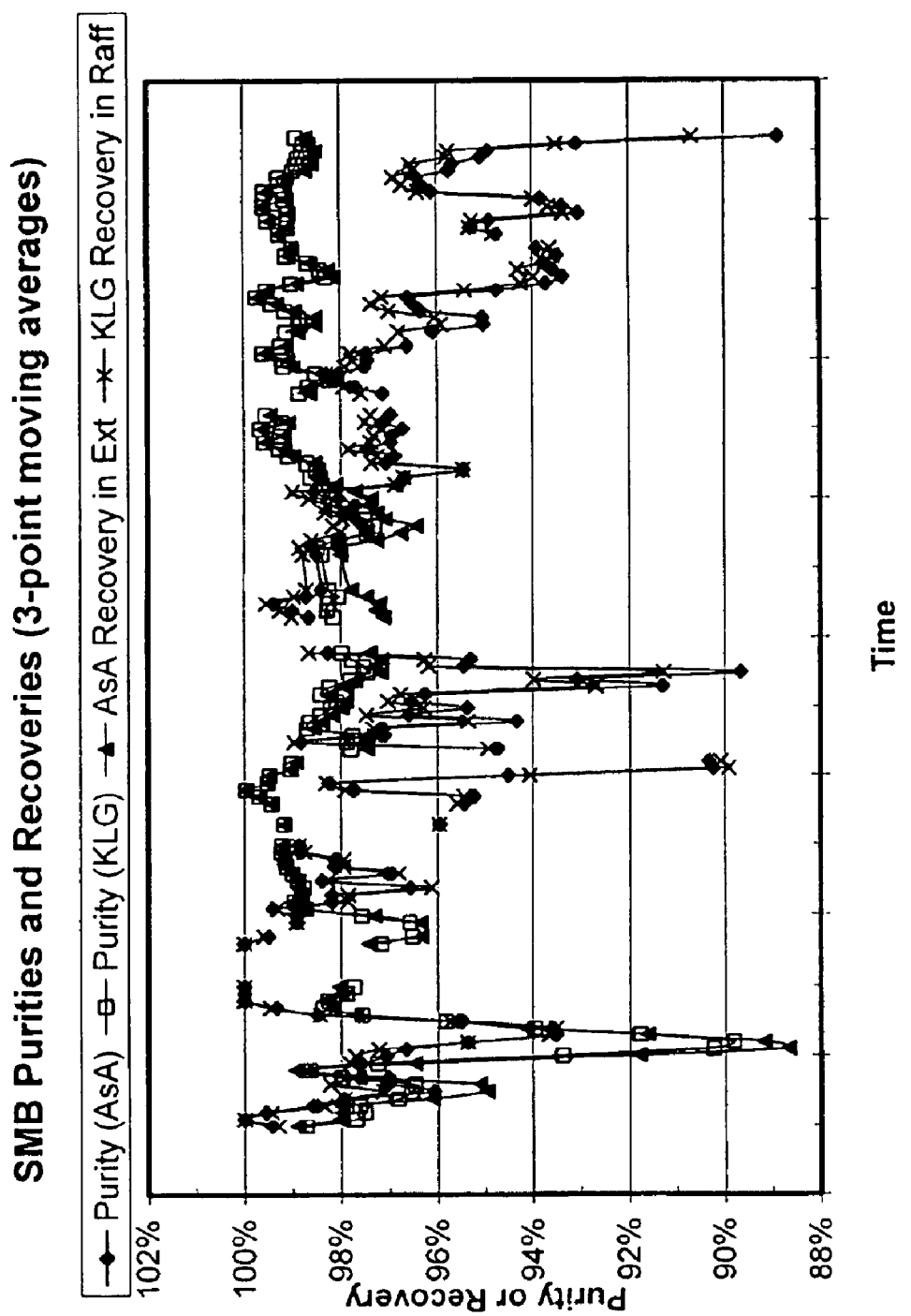
FIG. 9 shows purities and recoveries for L-ascorbic acid (AsA) and 2-keto-L-gulonic acid (KLG) using SMB purification of a post-reaction reaction solution of AsA and KLG recovered from a continuous reactor system in accordance with an embodiment of the present invention.

It was found that the SMB chromatography provided a very efficient separation of KLG and AsA, which was well adapted to the continuous system. Thus, as analyzed by HPLC, the purity of the AsA extract was consistently over 88%, and was generally greater than 93% (based on a KLG/AsA only basis) (FIG. 9). In addition, the purity of the KLG raffinate was consistently greater than 90%, and generally greater than 96%.

Overall, the recovery of AsA from the SMB chromatography separation (on a wt. % basis) was consistently greater than 88% and generally was found to be greater than 96%. The recovery of KLG was also highly efficient, with most samples approximating over 93% recovery (FIG. 9).

These purities are on a KLG/AsA only basis, and therefore, exclude water as well as non-volatile impurities arising from the KLG feed broth or reactor by-products. Generally, these impurities accounted for about 25 to 30 wt % of the total solids in the extract and raffinate products. In addition, calculations for recovery were normalized to the amount of KLG and AsA leaving the SMB unit (i.e. on an $KLG_{out}/AsA_{out}$ basis) and therefore, do not account for loss in the SMB unit itself. Still, overall it was found that the separation of KLG and AsA is so effective that the AsA purity in the extract is nearly identical to the KLG recovery in the raffinate.

The invention has been described in detail with particular reference to preferred embodiments thereof, but it will be understood that variations and modifications can be effected within the spirit and scope of the invention. References cited herein are incorporated in their entirety by reference unless otherwise noted.

What is claimed is:

1. A continuous process for manufacturing L-ascorbic acid comprising the steps of:
   (a) heating an aqueous solution of a starting material comprising 2-keto-L-gulonic acid or a derivative of 2-keto-L-gulonic acid at a temperature of about 120° C. to about 185° C. in a reactor in the presence of at least one sulfite species under conditions such that L-ascorbic acid is generated;
   (b) continuously removing from the reactor a post-reaction solution comprising unreacted starting material and L-ascorbic acid;
   (c) removing at least a portion of sulfur containing compounds from the post reaction solution;
   (d) removing at least a portion of the L-ascorbic acid from the post reaction solution; and
   (e) recycling unreacted starting material back to the reactor.

2. The method of claim 1, wherein the sulfite species comprises $SO_2$, $HSO_3^-$, $S_2O_3^{2-}$, $SO_3^{2-}$, $S_2O_4^{2-}$, and $S_2O_5^{2-}$.

3. The method of claim 2, wherein the sulfite species comprises sulfurous acid.

4. The method of claim 1, wherein the sulfite species comprises a catalyst for the conversion of 2-keto-L-gulonic acid to L-ascorbic acid.

5. The method of claim 1, wherein the sulfite is added to a final concentration comprising a range of 0.5% to 50% by moles relative to the 2-keto-L-gulonic acid compound.

6. The method of claim 1, wherein the sulfite is added to a final concentration comprising a range of 1% to 20% by moles relative to the 2-keto-L-gulonic acid compound.

7. The method of claim 1, wherein the starting material comprises an aqueous solution from a fermentation process for producing 2-keto-L-gulonic acid.

8. The method of claim 1, wherein the starting material comprises an aqueous solution of 2-keto-L-gulonic acid derived from the hydrolysis of the bisacetonide of 2-keto-L-gulonic acid or the esters of 2-keto-L-gulonic acid.

9. The method of claim 1, wherein the starting material comprises an aqueous solution of 1 to 40 weight percent 2-keto-L-gulonic acid.

10. The method of claim 1, wherein the starting material comprises an aqueous solution of 5 to 30 weight percent 2-keto-L-gulonic acid.

11. The method of claim 1, wherein the starting material comprises an aqueous solution of 8 to 15 weight percent 2-keto-L-gulonic acid.

12. The method of claim 1, wherein the conversion of 2-keto-L-gulonic acid substrate to L-ascorbic acid product preferably ranges from 5 to 95%.

13. The method of claim 1, wherein the conversion of 2-keto-L-gulonic acid substrate to L-ascorbic acid product ranges from 20 to 75%.

14. The method of claim 1, wherein the conversion of 2-keto-L-gulonic acid substrate to L-ascorbic acid product ranges from 30 to 60%.

15. The method of claim 1, wherein the sulfur containing compounds of step (c) comprise residual sulfite and/or sulfite bound by-products.

16. The method of claim 1, wherein the sulfur containing compounds of step (c) comprise sulfate.

17. The method of claim 1, wherein step (c) comprises removing sulfur containing compounds by adsorption with a solid matrix.

18. The method of claim 17, further comprising activated carbon as the adsorption matrix.

19. The method of claim 17, further comprising ion exchange resin as the adsorption matrix.

20. The method of claim 1, wherein step (d) comprises continuously separating L-ascorbic acid from unreacted 2-keto-L-gulonic acid in the post reaction solution to form an L-ascorbic acid rich solution and a solution rich in 2-keto-L-gulonic acid compound.

21. The method of claim 20, further comprising the step of separating the L-ascorbic acid from the L-ascorbic acid rich solution by crystallization.

22. The method of claim 20, wherein on a 2-keto-L-gulonic acid and ascorbic acid only basis, the ascorbic-acid solution of step (d) is comprised of at least 75 weight percent of L-ascorbic acid.

23. The method of claim 20, wherein on a 2-keto-L-gulonic acid and ascorbic acid only basis, the ascorbic-acid solution of step (d) is comprised of at least 85 weight percent of L-ascorbic acid.

24. The method of claim 20, wherein on a 2-keto-L-gulonic acid and ascorbic acid only basis, the ascorbic-acid solution of step (d) is comprised of at least 90 weight percent of L-ascorbic acid.

25. The method of claim 20, wherein on a 2-keto-L-gulonic acid and ascorbic acid only basis, the 2-keto-L-gulonic rich solution of step (d) is comprised of at least 75 weight percent of 2-keto-L-gulonic acid.

26. The method of claim 20, wherein on a 2-keto-L-gulonic acid and ascorbic acid only basis, the 2-keto-L-gulonic rich solution of step (d) is comprised of at least 85 weight percent of 2-keto-L-gulonic acid.

27. The method of claim 20, wherein on a 2-keto-L-gulonic acid and ascorbic acid only basis, the 2-keto-L-gulonic rich solution of step (d) is comprised of at least 90 weight percent of 2-keto-L-gulonic acid.

28. The method of claim 1, wherein steps (a) through (e) comprise at least a 50 mole percent yield of L-ascorbic acid.

29. The method of claim 1, wherein steps (a) through (e) comprise at least a 60 mole percent yield of L-ascorbic acid.

30. The method of claim 1, wherein the weight ratio of 2-keto-L-gulonic acid to L-ascorbic acid is from 0.1 to 10 in the post reaction solution.

31. The method of claim 1, wherein the weight ratio of 2-keto-L-gulonic acid to L-ascorbic acid is from 0.2 to 5 in the post reaction solution.

32. The method of claim 1, wherein the weight ratio of 2-keto-L-gulonic acid to L-ascorbic acid is from 1 to 3 in the post reaction solution.

33. The method of claim 1, wherein step (d) comprises separation of L-ascorbic acid from unreacted 2-keto-L-gulonic acid in the post reaction solution by crystallization, chromatography, or electrodialysis.

34. The method of claim 33, further comprising ion exclusion chromatography for separation of L-ascorbic acid from unreacted 2-keto-L-gulonic acid in the post reaction solution.

35. The method of claim 33, further comprising simulated moving bed (SMB) chromatography for separation of L-ascorbic acid from unreacted 2-keto-L-gulonic acid in the post reaction solution.

36. The method of claim 1, wherein steps (c) and (d) comprise simultaneous separation and removal of sulfur containing compounds including residual sulfite with the separation and segregation of L-ascorbic acid and unreacted 2-keto-L-gulonic acid.

37. The method of claim 36, further comprising ion exclusion chromatography.

38. The method of claim 36, further comprising five-zone simulated moving bed (SMB) chromatography.

39. The method of claim 1 wherein the starting material comprises 2-keto-L-gulonic acid, diacetone-2-keto-L-gulonic acid, or an ester of 2-keto-L-gulonic acid.

* * * * *